United States Patent [19]
Boebel et al.

[11] Patent Number: 5,669,927
[45] Date of Patent: Sep. 23, 1997

[54] INSTRUMENT FOR MORCELLATING

[75] Inventors: Manfred Boebel, Oetisheim; Hossein Messroghli, Groβ-Gerau, both of Germany

[73] Assignee: Richard Wolf GmbH, Knittlingen, Germany

[21] Appl. No.: 547,642

[22] Filed: Oct. 24, 1995

[30] Foreign Application Priority Data

Nov. 10, 1994 [DE] Germany .................. 44 40 035.7

[51] Int. Cl.⁶ .................. A61B 17/14; A61B 17/32; A61B 17/28
[52] U.S. Cl. .................. 606/180; 606/167; 606/205
[58] Field of Search .................. 606/1, 108, 167, 606/170, 171, 184, 185, 205, 211

[56] References Cited

U.S. PATENT DOCUMENTS

| | | |
|---|---|---|
| 4,174,715 | 11/1979 | Hasson . |
| 5,304,203 | 4/1994 | Mallawany et al. .................. 606/205 |
| 5,529,580 | 6/1996 | Kusunoki et al. .................. 606/180 |

FOREIGN PATENT DOCUMENTS

| | | |
|---|---|---|
| 1044979 | 12/1978 | Canada .................. 606/179 |
| 0555803 | 8/1993 | European Pat. Off. . |
| 1904590 | 6/1964 | Germany . |
| 3931577 | 4/1991 | Germany . |
| 9100873 | 5/1991 | Germany . |
| 4203622 | 8/1993 | Germany . |

*Primary Examiner*—Glenn Dawson
*Attorney, Agent, or Firm*—Panitch Schwarze Jacobs & Nadel, P.C.

[57] ABSTRACT

The instrument for morcellating, in particular for endosurgical operations, includes a tube with a cutter formed at its distal end which is the actual morcellator, and a gripping instrument introduced into this tube for holding the tissue to be removed. Between the gripping instrument and the cutting tube is provided a protective sheath into which the gripper of the gripping instrument is inserted before the beginning of the cutting procedure. This configuration reliably prevents fouling between the cutting instrument and the gripper.

13 Claims, 2 Drawing Sheets

INSTRUMENT FOR MORCELLATING

BACKGROUND OF THE INVENTION

This invention relates to an instrument for morcellating, in particular for use in endosurgical operations.

DESCRIPTION OF THE PRIOR ART

Such instruments are used for the removal of tissue, either for taking a specimen or for the removal of tissue parts per se and are increasingly used in endoscopic procedures. They comprise substantially a cutting tube, which is also known as a circular tube morcellator, which, for the purpose of cutting, is rotatable by means of an operating handle or a motor drive. Within this cutting tube is positioned a gripping instrument whose operating handle and gripper extend from the proximal and distal ends of the cutting tube respectively. The gripper is used to hold the tissue to be removed, and can be partly or fully retracted into the cutting tube.

A similar instrument with a motor driven cutting instrument is known from the document EP-A-0555803. The German utility model DE-U-9100873 discloses a cutting tube which is rotatably moveable by manual means. An instrument of this type is described in DE-A-4203622.

A problem with such known instruments is that it cannot always be ensured that the tissue removed is sufficiently soft and compressible to enable the gripper to be sufficiently closed, thus preventing fouling when the cutting tube is slid over it. It indeed often occurs that the arms of the gripper are so widely opened that the cutting tube is hindered from being slid forward, and the leading edge of the cutter abuts against the rear side of the gripper arms. Such a fouling results in the cutter being blunted, however it is more common that the cutter becomes completely ruined by its splaying out, and even the gripper becomes damaged.

SUMMARY OF THE INVENTION

For this reason it is an object of the invention to develop an instrument of this type such that by simple means of design any fouling between the gripper and cutting tube can be reliably prevented.

In accordance with the invention, this object is achieved by providing a protective sheath between the gripping instrument and cutting instrument. The gripper is pushed into the protective sheath before the actual cutting procedure ensuring that the arms are, at the latest, closed before the actual cutting procedure begins, and at the very least that they take up a position ensuring that the cutting tube can be slid over them without fouling. Thereby, using simple design means, any fouling with the gripper arms can be reliably prevented.

To ensure a sensitive control of the axial movement of the gripper with regard to the protective sheath, it is useful to provide a handle at the proximal end of the protective sheath or in this vicinity.

The cutting tube and protective sheath are dimensioned so as to enable the cutting tube to be freely rotatable and slidable over the protective sheath. The length of the cutting tube should also be smaller than the free length of the protective sheath, thereby allowing the cutting tube to be reliably secured on the protective sheath.

To enable the cutting tube to be moved finely and sturdily in both the axial and radial directions, it is useful to provide a circular handle at its proximal end. In the case of a motor drive, it is preferable to connect a separate handle.

In order to reliably ascertain from the proximal end that the gripper at the distal end is inserted into the protective sheath thereby eliminating the danger of a fouling between the gripper and the cutting tube, it is advantageous to provide a marker on the gripping instrument, for example on its shank, rather that on the instrument adjustment. For example a colored or geometric (radial notch or groove) marker can be made on the shank in such a way, that on pulling the gripping instrument from the protective sheath, the marker just becomes visible when the gripper is sufficiently inserted into the protective sheath, thus preventing its arms from fouling with the cutting tube. It is advantageous that the connection between the gripping instrument and the protective sheath be made in such a way that the gripping instrument and protective sheath are frictionally engaged with one another in this position i.e. during the subsequent cutting procedure only one of these two parts must be secured.

According to a further aspect of the invention, the distal end of the cutting tube is seperably attached to the remaining cutting tube, for example using a thread or bayonette connection. This permits the replacement of only the cutter of the cutting tube without having to replace the complete tube together with the handle, seal etc. In this case, if a fouling should occur by way of an operating error, or the cutter should become blunted or otherwise damaged, it can be replaced separately.

BRIEF DESCRIPTION OF THE DRAWINGS

The invention is hereinafter described in more detail by means of one embodiment of the invention represented in the drawings. These show.

DETAILED DESCRIPTION OF THE PREFERRED EMBODIMENTS

Figure 1:
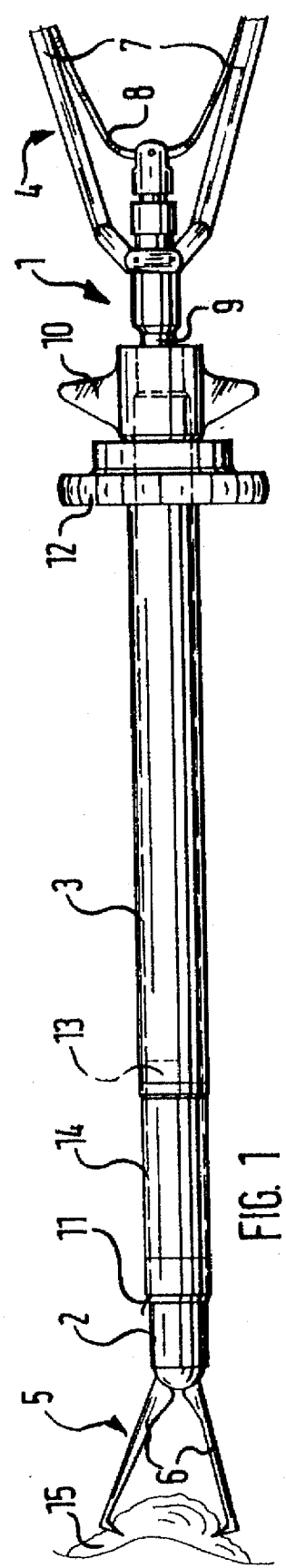
FIG. 1 a much simplified diagrammatic representation of a side view, shown partly in section, of the instrument according to the invention, in a first position, FIG. 2 the instrument according to FIG. 1 in a second position, FIG. 3 a longitudinal section of the cutting tube of the instrument, FIG. 4 a longitudinal section of the protective sheath of the instrument.

The instrument illustrated by the figures comprises a gripping instrument (1), a protective sheath (2) together with a cutting tube (3), the actual morcellator. The gripping instrument consists of a pincer like instrument with a handle (4) at its proximal end and a gripper (5) at its distal end. The gripper (5) has two arms (6) which can be operated by their respective operating handles (7). When the operating handles (7) are pushed together, the arms (6) close towards each other; movement in the opposite direction is effected by the force of a spring (8). The operating handles (7) are connected to one another by means of a mounting which is not shown but described in DE-A-393 1577, allowing the gripping instrument (1) to be automatically locked into a certain gripping position until it is disengaged from this position. The power transmission between the handle (4) and gripper (5) is effected by means of a long shank (9) in which a central rod is guided (not shown).

Figure 4:
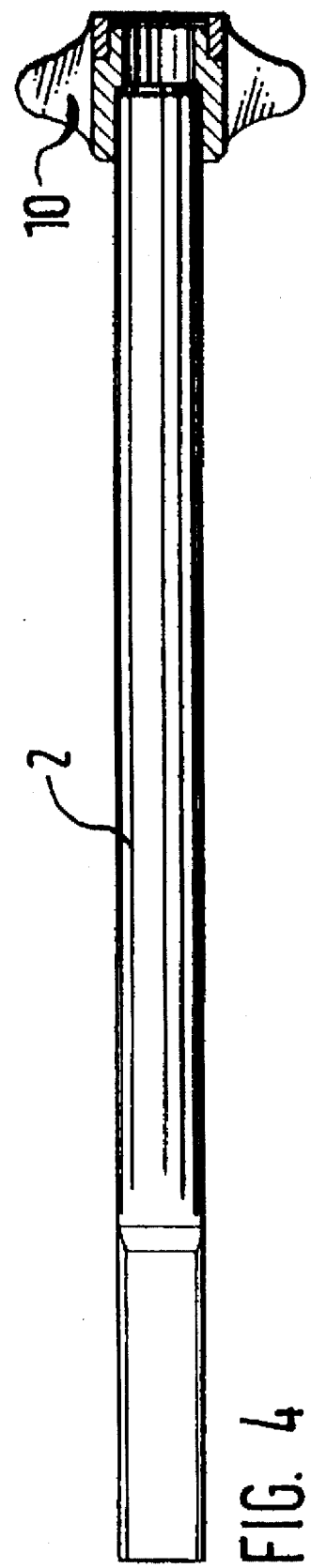

Along the shank (9) the gripping instrument (1) is surrounded by the protective sheath (2), which has a cylindrical outer contour. This protective sheath (2) is separately illustrated in FIG. 4. Its length approximately corresponds to the length of the shank (9) of the gripping instrument (1) and its inside diameter is so dimensioned as to allow the gripping instrument (1) with closed arms (5) together with the shank (9) to be inserted and thread through it. A ring-shaped handle (10) is situated at the proximal end of the instrument and the inside diameter in this proximity is slightly reduced and where appropriate a radial seal may be provided. The distal end of the protective sheath (2) is reinforced over a certain length which corresponds to or is slightly larger than the length of the gripper (5), i.e. the inside diameter is reduced here.

The distal leading edge of the cutting tube (3) is formed as a cutter (11) and comprises a ring-shaped handle (12) at its proximal end. In the proximity of the handle there is an internal radial seal (not shown). The cutting tube (3) has a length which is shorter than the free length of the protective sheath (2) on which it sits, from the protective sheath's handle (10) to its distal end. The cutting tube comprises substantially a cylindrical outer contour, which is provided with a thread connection (13) at its distal end, enabling the replacement of the distal end part (14) together with the cutter (11). The end part (14) comprises an external thread which can be screwed onto the corresponding internal thread of the cutting tube (3).

Figure 2:
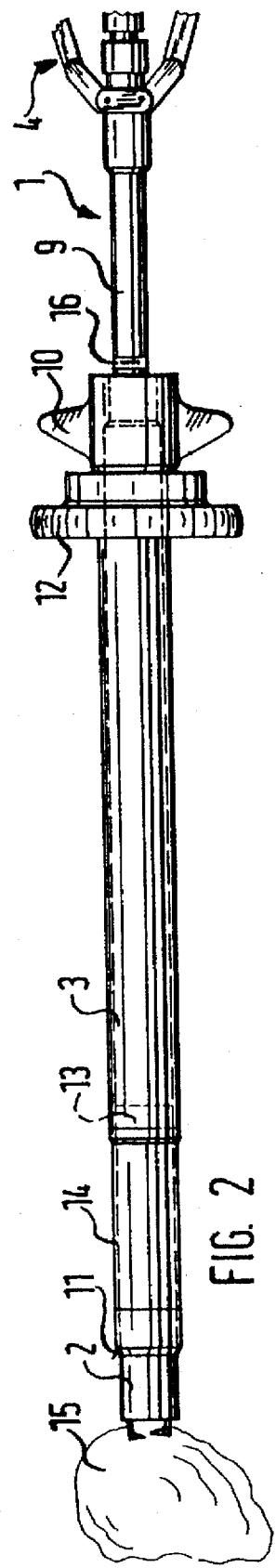
Figure 3:
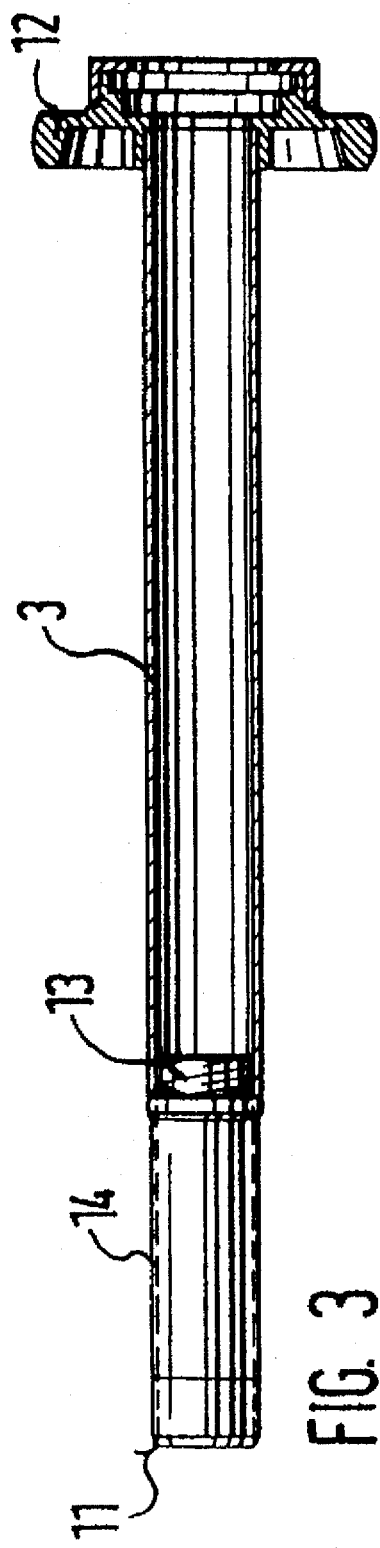

The instrument is assembled by first inserting the gripping instrument (1) together with the gripper (5) through the protective sheath (2) already accomodating the cutting tube (3), resulting in the configuration of the instrument shown in FIG. 1. This instrument is for example directed into the body by way of a trocar tube or opening in the body, until it reaches the area from which the tissue is to be removed. This tissue, given the reference numeral (15) in the figures, is then collected by the gripper (5) by manually closing the operating handles (7). The gripping instrument (1) is then pulled from the protective sheath (2) until a marker (16) in the form of a radial notch made on the shank (9) becomes visible. The marker (16) is made in such a way as to just become visible when the gripper (5) is almost completely inserted (retracted) into the protective sheath (2) i.e. the gripper (5) can no longer foul with the cutting tube (3). In this position, when the marker (16) becomes visible, by design there is an increased friction fit between the shank (9) of the gripping instrument (1) and the protective sheath (2), thus automatically fixing the instrument in this position (FIG. 2).

The handle (12) of the cutting tube (3) is then moved towards the tissue (15) and the actual cutting process is effected by rotating the handle (12). It is thereby ensured that the gripper (5) is inserted into the protective sheath (2) thus preventing any fouling between the cutting tube (3) and the gripper (5).

The removal of the tissue together with the instrument is then carried out in the usual manner, already known per se.

What is claimed is:

1. An instrument for morcellating, in particular for endosurgical operation, comprising a cutting tube (3) having a distal end formed as a cutter (11) which can be rotated and axially moved from said tube's proximal end, a gripping instrument (1) arranged inside the tube (3), said gripping instrument comprising a distal gripper (5) and a proximal handle (4) connected by a hollow shank (9), characterized in that there is a protective sheath (2) arranged between the gripping instrument (1) and the cutting tube (3), wherein the protective sheath is a separate piece from the gripping instrument, and the gripping instrument is insertable through and removable from the protective sheath.

2. An instrument according to claim 1 characterized in that the protective sheath (2) comprises a handle (10) at its distal end.

3. An instrument according to claim 2 characterized in that the cutting tube (3) is freely rotatably and slidably mounted over the protective sheath (2).

4. An instrument according to claims 1 characterized in that the cutting tube (3) is freely rotatably and slidably mounted over the protective sheath (2).

5. An instrument according to claim 1 characterized in that the cutting tube (3) has a length which is smaller than a length of the protective sheath (2).

6. An instrument according to claim 1 characterized in that the cutting tube (3) comprises a ring shaped handle (12) at its proximal end.

7. An instrument according to claim 1 characterized in that a marker (16) is located on the gripping instrument (1), such that a distal position of the gripper relative to a distal end of the protective sheath can be recognized from a proximal end of the instrument.

8. An instrument according to claim 1 characterized in that a distal end part (14) of the cutting tube (3) is detachable from a remaining part of the cutting tube (3).

9. An instrument according to claim 8, wherein the distal end part (14) is detachable from the remaining part of the cutting tube (3) by means of a thread.

10. An instrument according to claim 8, wherein the distal end part (14) is detachable from the remaining part of the cutting tube (3) by means of a bayonette attachment.

11. An instrument according to claim 1, characterized in that in a position in which the gripper (5) has just been retracted into the protective sheath (2), the gripping instrument (1) is fixed to the protective sheath (2) by a friction fit.

12. An instrument for morcellating, in particular for endosurgical operation, comprising a cutting tube (3) having a distal end formed as a cutter (11) which can be rotated and axially moved from said tube's proximal end, a gripping instrument (1) arranged inside the tube (3), said gripping instrument comprising a distal gripper (5) and a proximal handle (4), characterized in that there is a protective sheath (2) arranged between the gripping instrument (1) and the cutting tube (3), wherein the protective sheath is a separate piece from the gripping instrument, and the gripping instrument is insertable through and removable from the protective sheath, and wherein the protective sheath is reinforced at a distal end by a thickened wall and reduced internal diameter, the reinforcement corresponding approximately in length to the gripper (5).

13. An instrument for morcellating, in particular for endosurgical operation, comprising a cutting tube (3) having a distal end formed as a cutter (11) which can be rotated and axially moved from said tube's proximal end, a gripping instrument (1) arranged inside the tube (3), said gripping instrument comprising a distal gripper (5) and a proximal handle (4), characterized in that there is a protective sheath (2) arranged between the gripping instrument (1) and the cutting tube (3), wherein the protective sheath is a separate piece from the gripping instrument, and the gripping instrument is insertable through and removable from the protective sheath, wherein the gripping instrument is one in which the distal gripper (5) is closed and opened by pushing operating handles (7) of the proximal handle (4) together and apart.

* * * * *